United States Patent [19]

Opgenorth et al.

[11] 4,255,333

[45] Mar. 10, 1981

[54] PREPARATION OF INDOLENINES

[75] Inventors: Hans-Joachim Opgenorth, Frankenthal; Horst Scheuermann, Ludwigshafen; Harald Laas, Maxdorf; Axel Nissen, Leimen, all of Fed. Rep. of Germany

[73] Assignee: BASF Aktiengesellschaft, Ludwigshafen, Fed. Rep. of Germany

[21] Appl. No.: 7,773

[22] Filed: Jan. 30, 1979

[30] Foreign Application Priority Data

Feb. 10, 1978 [DE] Fed. Rep. of Germany ....... 2805620

[51] Int. Cl.³ .................. C07D 209/08; C07C 119/10
[52] U.S. Cl. ................................. 260/319.1; 564/276
[58] Field of Search .......................... 260/319.1, 566 F

[56] References Cited

FOREIGN PATENT DOCUMENTS 2514759  9/1975  Fed. Rep. of Germany .

OTHER PUBLICATIONS

R. C. Fuson, "Adv. Org. Chem.", pp. 18-21, and 58-61, Wiley, N.Y., (1950).
Elderfield, "Heterocyclic Compounds", vol. 3, Chapman & Hall, Ltd., New York, N.Y., (1952), pp. 97-98.

Primary Examiner—Jose Tovar
Assistant Examiner—D. B. Springer
Attorney, Agent, or Firm—Oblon, Fisher, Spivak, McClelland & Maier

[57] ABSTRACT

A process for the preparation of an indolenine of the formula

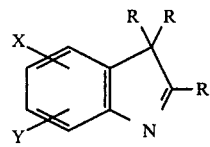

where R, X and Y are conventional substituents, by thermal rearrangement of a compound of the formula

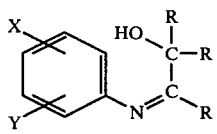

to give a compound of the formula

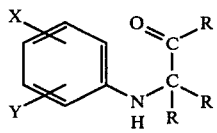

and cyclization of this compound in the presence of an acid catalyst.

8 Claims, No Drawings

PREPARATION OF INDOLENINES

The present invention relates to a process for the preparation of a compound of the formula I

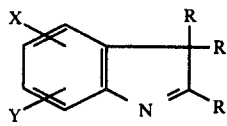

where, independently of one another, R is alkyl or benzyl, X is hydrogen, chlorine, cyano, bromine, $C_1$-$C_4$-alkyl, $C_1$-$C_4$-alkoxy, $C_1$-$C_4$-alkoxycarbonyl, nitro or $C_1$-$C_4$-alkylsulfonyl and Y is hydrogen, chlorine, bromine or methyl, wherein a compound of the formula

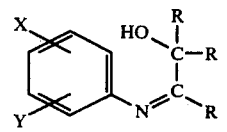

is thermally rearranged to give a compound of the formula III

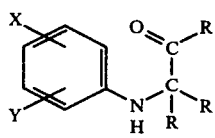

which is then cyclized in the presence of an acid catalyst to give a compound of the formula I.

In a particularly preferred process, the compound of the formula II, ie. the Schiff base, is prepared from a compound of the formula IV

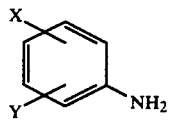

and a compound of the formula V

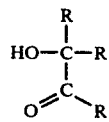

by condensation in the presence of an azeotrope-forming solvent and of an acid catalyst, the catalyst is then removed or inactivated, the solvent and any unconverted starting materials are substantially distilled off and the residue is then subjected to thermal rearrangement and cyclization.

Alkyl R is in particular of 1 to 4 carbon atoms, methyl being preferred.

Examples of azeotrope-forming solvents for use in the reaction of the compounds of the formulae IV and V are hydrocarbons and chlorohydrocarbons, eg. benzene, cyclohexane, methylcyclohexane, chlorobenzene and, preferably, toluene and xylenes.

For the purposes of the invention, an acid catalyst for the preparation of a compound of the formula II is a compound which catalyzes the formation of the compound of the formula II but can subsequently be removed or inactivated. Volatile catalysts which can be distilled off together with the azeotrope-forming solvent are preferred; examples of these are formic acid, chloroacetic acid, butyric acid and especially acetic acid and propionic acid. Further suitable catalysts are compounds which can, for example, be inactivated by forming an amide with an amine of the formula IV. Acidic ion exchangers which can subsequently be filtered off are also suitable catalysts.

Suitable catalysts for the cyclization of a compound of the formula III to give a compound of the formula I are Lewis acids, eg. zinc chloride, aluminum chloride and boron trifluoride, organic acids, eg. acetic acid, propionic acid, chloroacetic acid, benzoic acid, stearic acid, benzene-sulfonic acid, toluenesulfonic acid, succinic acid, glutaric acid and adipic acid, acidic salts, eg. sodium bisulfate and sodium dihydrogen phosphate, and mineral acids, eg. phosphorous acid, phosphoric acid and, preferably, hydrochloric acid and sulfuric acid. It has proved particularly advantageous to employ such catalysts in the form of their salts with the amines of the formula IV.

The reaction of the compounds of the formulae IV and V is advantageously carried out by using an excess of amine, up to a molar ratio of amine to hydroxyketone of ~2:1 and heating the components (compound IV, compound V, catalyst and solvent), with azeotropic removal of the water. The solvent is as a rule employed in an amount of from 1 to 5 parts by weight per part by weight of hydroxyketone, whilst the catalyst is employed in an amount of from about 0.1 to 10%, based on hydroxyketone.

In the case of the preferred use of a volatile catalyst, the preparation of the Schiff base is followed by distilling off the said catalyst and the solvent, as well as the greater part of the excess amine of the formula IV. Heating is then continued until the conversion of II to III (which can, for example, be followed by gas chromatography) is complete. The conversion is as a rule carried out at from 150° to 300° C., preferably from 200° to 250° C.

Thereafter the cyclization to give the compound of the formula I is advantageously carried out at from 100° to 250° C. or, in the case of the preferred catalysts, from 140° to 200° C. The required amount of catalyst is from 0.1 to 20 percent by weight, preferably from 1 to 10 percent by weight, based on hydroxyketone employed.

The cyclization takes place particularly readily in the presence of an amine of the formula IV. Hence, it is advantageous, after the formation of the Schiff base II, only to remove the excess amine to the point that an amount at least equivalent to the amount of catalyst used remains. However, an excess of amine over catalyst is in no way disadvantageous; rather, it accelerates the reaction. Since, however, the distillative separation of the amine IV from the indolenine I is, for example, more difficult than the distillative separation of the compounds of the formulae II and III, it is advantageous to adhere to only a slight excess of amine.

Details of how the reaction may be carried out are to be found in the Examples, where parts and percentages are by weight, unless stated otherwise.

The compounds of the formula I are important intermediates for the preparation of dyes, in particular after the nitrogen has been alkylated and the compound deprotonized to give a compound of the formula VI

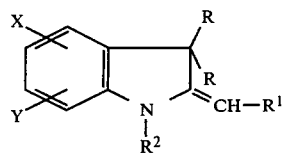

where $R^1$ is R minus one $CH_2$ group and $R^2$ is alkyl of 1 to 4 carbon atoms, hydroxyethyl, hydroxypropyl or benzyl.

The compounds of the formula I obtainable according to the invention can be alkylated directly, ie. without purification.

German Laid-Open Application DOS No. 2,514,759 discloses a process for the preparation of a compound of the formula I, in which process, however, the catalyst used for the formation of the Schiff base is present during all stages of the reaction. This entails substantial disadvantages in industrial operation, which are avoided in the process according to the invention:

1. The water formed in the reaction mixture on cyclization to give the compound of the formula I causes redissociation of the Schiff base, which leads to a reduction in yield, especially in the case of sizable batches, unless expensive precautionary measures are taken. This risk does not apply in the case of the process according to the invention, since the Schiff base II is first converted to compound III, which is not prone to hydrolyze.

2. The distillative removal of an excess of more than 1 mole of aniline per mole of indolenine requires an efficient column because of the low difference in boiling points, this being due to the fact that since the indolenine decomposes easily at elevated temperatures, the distillation should advantageously be carried out under reduced pressure. By contrast, in the case of the process according to the invention the excess amine can be separated from the higher-boiling compounds II and III by distillation under atmospheric pressure, so that it is not necessary to use a column.

EXAMPLE 1

408 parts of 2-methyl-2-hydroxy-butan-3-one, 558 parts of aniline and 20 parts of acetic acid in 650 parts of toluene are heated, with removal of water from the system, until no more water separates off. The volatile constituents are then distilled off until the internal temperature reaches 220° C. The distillate can be re-used, without further treatment, in a subsequent batch. The residue is kept for 5 hours at 220° C. and is then cooled to 160° C., and 40 parts of concentrated hydrochloric acid are added. After heating for a further three hours, during which the water formed distils off, the reaction is complete. The product is either directly processed further or distilled. 498 parts of 2,3,3-trimethyl-indolenine are obtained, corresponding to 78.5% of theory, based on 2-methyl-2-hydroxy-butan-3-one.

EXAMPLE 2

The procedure described in Example 1 is followed, but instead of 40 parts of hydrochloric acid 40 parts of concentrated sulfuric acid are added. 473 parts of 2,3,3-trimethyl-indolenine are obtained, corresponding to 74.4% of theory, based on 2-methyl-2-hydroxy-butan-3-one.

EXAMPLE 3

The procedure described in Example 1 is followed, but after heating for five hours the mixture is distilled under reduced pressure. 576 parts of 2-anilino-2-methyl-butan-3-one (melting point 65°–66° C.) are obtained, corresponding to 81.4% of theory, based on 2-methyl-2-hydroxy-butan-3-one.

EXAMPLE 4

246 parts of p-anisidine, 204 parts of 2-methyl-2-hydroxy-butan-3-one and 10 parts of acetic acid in 650 parts of toluene are heated, with removal of water from the system, until no more water separates off. The solvent is then distilled off and the residue is heated for 5 hours at 220° C. After cooling to 160° C., 10 parts of concentrated sulfuric acid are added; the mixture is kept at 160° C. for 3 hours, whilst distilling off the water formed. Distillation under reduced pressure (21 mbar) gives 318.7 parts of 5-methoxy-2,3,3-trimethyl-indolenine (melting point 53°–54° C.), corresponding to 84.3% of theory.

The following indolenine derivatives are obtained by similar methods:

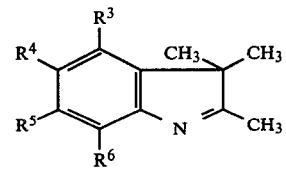

| Example | $R^3$ | $R^4$ | $R^5$ | $R^6$ | Yield |
| --- | --- | --- | --- | --- | --- |
| 5 | H | Cl | H | H | 75.6 |
| 6 | H | H | Cl | $CH_3$ | 71.4 |
| 7 | H | $CH_3$ | H | H | 77.4 |
| 8 | H | Br | H | H | 73.9 |
| 9 | H | H | H | CN | 55.6 |
| 10 | H | $SO_2CH_3$ | H | H | 64.6 |
| 11 | H | $OC_2H_5$ | H | H | 72.3 |
| 12 | H | $OC_4H_9$ | H | H | 69.4 |

We claim:

1. A process for the preparation of an indolenine of the formula:

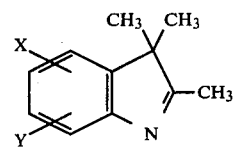

wherein, independently of one another, X is hydrogen, chlorine, bromine, cyano, $C_1$–$C_4$ alkyl, $C_1$–$C_4$ alkoxy, $C_1$–$C_4$ alkoxycarbonyl, nitro or $C_1$–$C_4$ alkylsulfonyl and Y is hydrogen, chlorine, bromine or methyl, comprising:

thermally rearranging a Schiff base of the formula (II)

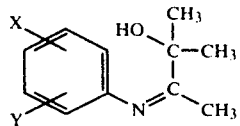

at a temperature of 150° to 300° C. to a compound of the formula (III)

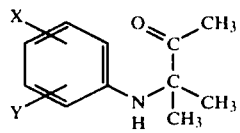

and cyclizing said compound (III) to said indolenine at a temperature of 100° to 250° C. in the presence of a catalyzing amount of an acid catalyst sufficient to effect said cyclization.

2. The process of claim 1, wherein acid cyclization catalyst is an acid selected from the group consisting of zinc chloride, aluminum chloride, boron trifluoride, acetic acid, propionic acid, chloroacetic acid, benzoic acid, stearic acid, benzenesulfonic acid, toluenesulfonic acid, succinic acid, glutaric acid, adipic acid, sodium bisulfate, sodium dihydrogenphosphate, phosphoric acid, hydrochloric acid, sulfuric acid and phosphorous acid.

3. The process of claim 2, wherein said acid cyclization catalyst is hydrochloric acid or sulfuric acid.

4. The process of claim 1, which further comprises: preparing said compound (II) by reacting an aniline compound of the formula (IV)

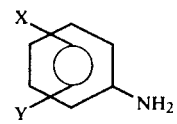

wherein X, Y and R are as defined above with 2-methyl-2-hydroxybutanone in a water azeotrope forming solvent in the presence of an acid catalyst sufficient to promote the reaction;
removing or inactivating said catalyst; and
distilling said solvent and unconverted aniline compound and/or hydroxyketone compound from said Schiff base product.

5. The process of claim 4, wherein said acid catalyst for the Schiff base reaction is a volatile carboxylic acid.

6. The process of claim 4, wherein the mole ratio of said aniline compound to said hydroxyketone compound is about 2:1.

7. The process of claim 4, wherein said acid catalyst for said Schiff base forming reaction is present in an amount of about 0.1 to 10% by weight based on said hydroxyketone compound.

8. The process of claim 4, wherein said water azeotrope forming solvent is a compound selected from the group consisting of benzene, cyclohexane, methylcyclohexane, chlorobenzene, toluene and xylene.

* * * * *